US00PP17497P2

(12) United States Plant Patent
Parthasarathy et al.

(10) Patent No.: US PP17,497 P2
(45) Date of Patent: Mar. 13, 2007

(54) ***AGLAONEMA* PLANT NAMED 'GOLD DUST'**

(50) Latin Name: *Aglaonema hybrida*
Varietal Denomination: Gold Dust

(76) Inventors: Gopalaswamy Parthasarathy, "Srinivasa", 237/46, Fifth Main Road, Chamrajpet, Bangalore 560018 (IN); Parthasarathy Mukundan, "Srinivasa", 237/46, Fifth Main Road, Chamrajpet, Bangalore 560018 (IN)

( * ) Notice: Subject to any disclaimer, the term of this patent is extended or adjusted under 35 U.S.C. 154(b) by 25 days.

(21) Appl. No.: 11/174,970

(22) Filed: Jul. 5, 2005

(51) Int. Cl.
*A01H 5/00* (2006.01)

(52) U.S. Cl. ..... Plt./376

(58) Field of Classification Search ..... Plt./376
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Aglaonema* plant named 'Gold Dust', characterized by its upright and outwardly arching plant form; vigorous growth habit; freely clumping habit and relatively short internodes; full, dense and bushy appearance; large ovate leaves with acuminate apices; upper leaf surfaces dark green in color with random yellow green and pale yellow-colored spots and blotches and a few scattered dark green-colored spots and blotches; lower leaf surfaces pale green in color with random yellow green and pale yellow-colored spots and blotches; dark green-colored leaf petioles; petiole wings dark green with random pale yellow spots and blotches; and tolerance to low temperatures.

1 Drawing Sheet

Botanical designation: *Aglaonema hybrida.*
Cultivar denomination: 'Gold Dust'.

BACKGROUND OF THE INVENTION

The present Invention relates to a new and distinct cultivar of *Aglaonema* plant, botanically known as *Aglaonema hybrida* and hereinafter referred to by the name 'Gold Dust'.

The new *Aglaonema* is the result of a planned breeding program conducted by the Inventors in Chamrajpet, Bangalore, India. The objective of the breeding program is to create new vigorous *Aglaonema* cultivars with compact and dense plant habit, unique leaf coloration, interesting leaf shapes, resistance to pathogens and pests common to *Aglaonemas* and tolerance to low temperatures.

The new *Aglaonema* originated from a cross-pollination made by the Inventors on Apr. 12, 1984 of the *Aglaonema brevispathum* (Engl.) Jervis *f. hospitum* (F.N.Wms.) Nicols, cultivar Variablis, not patented, as the female, or seed, parent with the *Aglaonema commutation* var. *maculatum* cultivar Malay Lady, not patented, as the male, or pollen, parent. The new *Aglaonema* was discovered and selected by the Inventors in 1985 as a single plant within the progeny of the stated cross-pollination in a controlled environment in Chamrajpet, Bangalore, India. The new *Aglaonema* was selected on the basis of its plant habit, leaf shape and uniquely colored foliage.

Asexual propagation of the new cultivar by divisions and cuttings since September, 1986 in a controlled environment in Chamrajpet, Bangalore, India, has shown that the unique features of this new *Aglaonema* are stable and reproduced true to type in successive generations.

SUMMARY OF THE INVENTION

The following traits have been repeatedly observed and are determined to be the unique characteristics of 'Gold Dust'. These characteristics in combination distinguish 'Gold Dust' as a new and distinct cultivar of *Aglaonema:*

1. Upright and outwardly arching plant form.
2. Vigorous growth habit.
3. Freely clumping habit and relatively short internodes; full, dense and bushy appearance.
4. Large ovate leaves with acuminate apices.
5. Unique leaf coloration; upper leaf surfaces dark green in color with random yellow green and pale yellow-colored spots and blotches and a few scattered dark green-colored spots and blotches; lower leaf surfaces pale green in color with random yellow green and pale yellow-colored spots and blotches.
6. Dark green-colored leaf petioles; petiole wings dark green with random pale yellow spots and blotches.
7. Tolerant to low temperatures.

In side-by-side comparisons conducted by the Inventors in Chamrajpet, Bangalore, India, plants of the new *Aglaonema* differed from plants of the female parent, the cultivar Variabilis, in the following characteristics:

1. Plants of the new *Aglaonema* were more freely clumping and denser than plants of the cultivar Variabilis.
2. Leaves of plants of the new *Aglaonema* were lighter in color than leaves of plants of the cultivar Variabilis.
3. Plants of the new *Aglaonema* had longer and lighter green-colored leaf petioles than the cultivar Variabilis.

In side-by-side comparisons conducted by the Inventors in Chamrajpet, Bangalore, India, plants of the new *Aglaonema* differed from plants of the male parent, the cultivar Malay Lady, in the following characteristics:

1. Plants of the new *Aglaonema* were more compact and more outwardly arching than plants of the cultivar Malay Lady.
2. Plants of the new *Aglaonema* were more freely clumping and denser than plants of the cultivar Malay Lady.

3. Leaves of plants of the new *Aglaonema* were broader than and not as undulate as leaves of plants of the cultivar Malay Lady.
4. Plants of the new *Aglaonema* and the cultivar Malay Lady differed in leaf coloration.

Plants of the new *Aglaonema* can be compared to plants of the cultivar Emerald Star, disclosed in U.S. Plant Pat. No. 10,659. In side-by-side comparisons conducted in Chamrajpet, Bangalore, India, plants of the new *Aglaonema* differed from plants of the *Aglaonema* cultivar Emerald Star in the following characteristics:

1. Plants of the new *Aglaonema* had shorter internodes than plants of the cultivar Emerald Star.
2. Leaves of plants of the new *Aglaonema* were broader than leaves of plants of the cultivar Emerald Star.
3. Plants of the new *Aglaonema* and the cultivar Emerald Star differed in leaf coloration as plants of the cultivar Emerald Star had darker green-colored leaves.
4. Plants of the new *Aglaonema* and the cultivar Emerald Star differed in leaf petiole coloration as plants of the cultivar Emerald Star had dark green-colored petioles with sparse white-colored spots.

Plants of the new *Aglaonema* can also be compared to plants of the cultivar Stars, disclosed in U.S. Plant Pat. No. 10,247. In side-by-side comparisons conducted in Chamrajpet, Bangalore, India, plants of the new *Aglaonema* differed from plants of the *Aglaonema* cultivar Stars in the following characteristics:

1. Plants of the new *Aglaonema* were more compact and had shorter internodes than plants of the cultivar Stars.
2. Plants of the new *Aglaonema* were more freely clumping and denser than plants of the cultivar Stars.
3. Plants of the new *Aglaonema* had broadly ovate leaves whereas plants of the cultivar Stars had broadly ovate leaves.
4. Plants of the new *Aglaonema* and the cultivar Stars differed in leaf coloration as plants of the cultivar Stars had darker green-colored leaves.

BRIEF DESCRIPTION OF THE PHOTOGRAPH

The accompanying colored photograph illustrates the overall appearance of the new *Aglaonema,* showing the colors as true as it is reasonably possible to obtain in colored reproductions of this type. Colors in the photograph may differ slightly from the color values cited in the detailed botanical description which accurately describe the colors of the new *Aglaonema.* The photograph comprises a side perspective view of a typical plant of 'Gold Dust'.

DETAILED BOTANICAL DESCRIPTION

The cultivar Gold Dust has not been observed under all possible environmental conditions. The phenotype may vary somewhat with variations in environment such as temperature and light intensity without, however, any variance in genotype.

The following observations and measurements describe plants of the new *Aglaonema* that were grown in 25-cm containers, in Homestead, Fla., in a polypropylene-covered shadehouse with light levels about 2,500 foot-candles. During the production of the plants, temperatures ranged from 2 to 43° C. Plants used for the photograph and description were about 14 months from planting. Color references are made to The Royal Horticultural Society Colour Chart, 1995 Edition, except where general terms of ordinary dictionary significance are used.

Botanical classification: *Aglaonema hybrida* cultivar Gold Dust.

Parentage:

*Female, or seed, parent.*—*Aglaonema brevispathum* (Engl.) Jervis *f. hospitum* (F.N.Wms.) Nicols. cultivar Variablis, not patented. Male, or pollen, parent: *Aglaonema commutatum* var. *maculatum* cultivar Malay Lady, not patented.

Propagation:

*Type.*—By divisions.

*Time to initiate roots.*—Summer: About 18 to 20 days at 25 to 36° C. Winter: About 30 to 35 days at 15 to 28° C.

*Time to produce a rooted plant.*—Summer: About 30 to 35 days at 25 to 36° C. Winter: About 40 to 45 days at 15 to 28° C.

*Root description.*—Thick, fibrous, fleshy; off-white in color.

*Rooting habit.*—Freely-branching; dense.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 25-cm containers.

*Growth habit.*—Freely clumping habit; plants typically produce about four offshoots per plant; full, dense and bushy appearance.

*Plant height.*—About 51 cm.

*Plant width* (*spread*).—About 57 cm.

*Stem description.*—Length: About 21 cm. Diameter: About 1.9 cm. Internode length: About 1.2 cm. Aspect: Upright. Strength: Good. Color: Darker green than 147A.

*Foliage description.*—Appearance: Single; clasping. Length: About 24.5 cm. Width: About 12 cm. Shape: Ovate. Apex: Acuminate. Base: Obtuse. Margin: Entire; undulating. Orientation: Initially upright to roughly horizontal; twisting. Texture, upper and lower surfaces: Smooth, glabrous; thick and leathery; rugose. Veins: Slightly recessed on upper surface and prominent on lower surface. Venation pattern: Pinnate. Color: Developing leaves, upper surface: Ground color, close to 146B; random spots and blotches, close to 147A and close to 4D or 5D. Developing leaves, lower surface: Ground color, close to 147B; random spots and blotches, close to 4D to 5D. Fully expanded leaves, upper surface: Ground color, close to 147A; random spots and blotches, 144A, close to 4D and darker green than 147A; midvein, darker green than 147A; lateral veins, similar to lamina. Fully expanded leaves, lower surface: Ground color, close to 147A; random spots and blotches, 144A and close to 4D; venation similar to lamina. Petiole: Aspect: Erect to slightly bent. Length: About 14.75 cm. Diameter, distal: About 1.75 cm. Diameter, proximal: About 4 mm. Wing length: About 6.1 cm. Wing diameter: About 6 mm. Color: Developing leaves, petiole and wing: Close to 144B. Fully expanded leaves, petiole: 147A. Fully expanded leaves, wing: 147A; random spots and blotches, close to 4D.

Inflorescence description: Inflorescence development has not been observed on plants of the new *Aglaonema* grown under shadehouse production conditions.

Disease/pest resistance: Plants of the new *Aglaonema* have been observed to be resistant to pathogens common to *Aglaonema* such as *Xanthomonas* and *Phytophthora*. Plants of the new *Aglaonema* have not been observed to be resistant to pests and other pathogens common to *Aglaonema*.

Weather tolerance: Plants of the new *Aglaonema* have been observed to be tolerant to wind, rain and temperatures ranging from 2 to 43° C.

It is claimed:

1. A new and distinct cultivar of *Aglaonema* plant named 'Gold Dust', as illustrated and described.

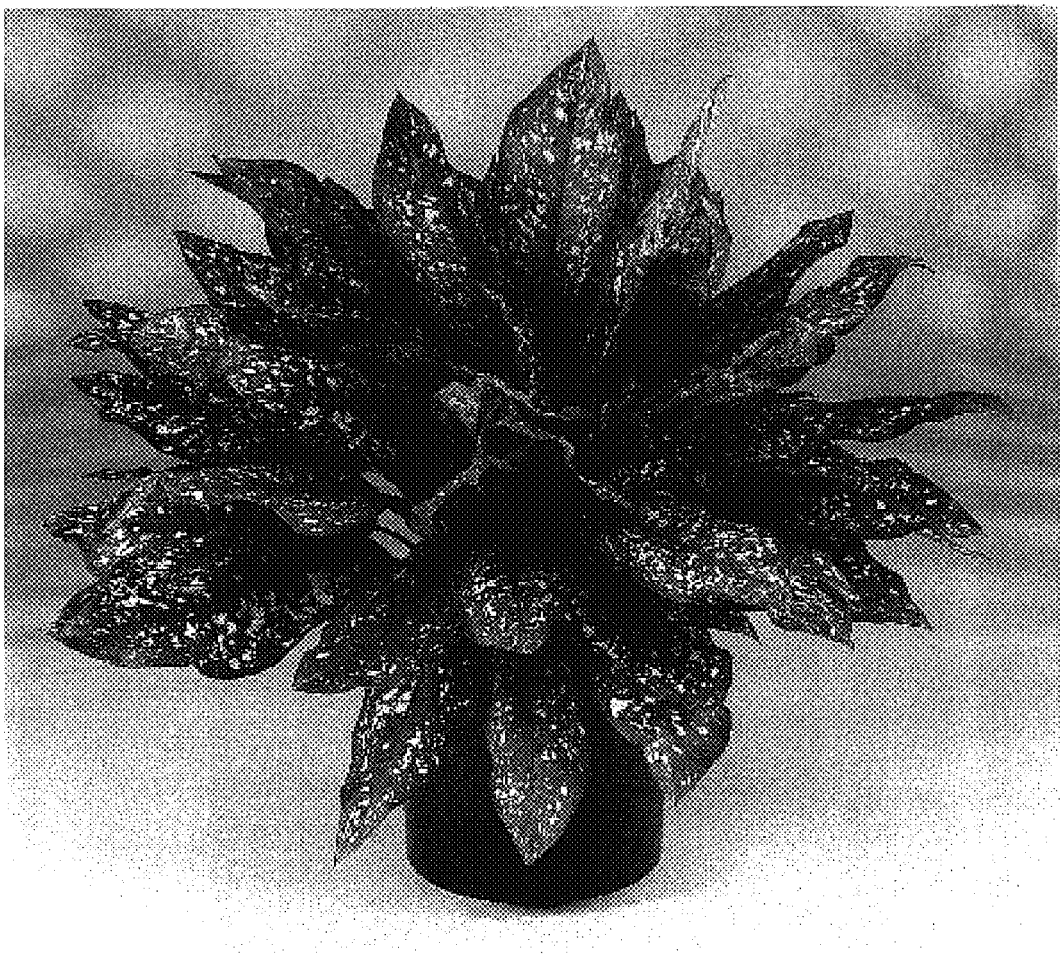

* * * * *